United States Patent [19]

Rich

[11] Patent Number: 5,145,607
[45] Date of Patent: Sep. 8, 1992

[54] OPTICALLY CLEAR CONDITIONING SHAMPOO COMPRISING ANIONIC AND CATIONIC SURFACTANTS

[75] Inventor: Arthur G. Rich, Spring Valley, N.Y.

[73] Assignee: Takasago International Corporation (U.S.A.), Rockleigh, N.J.

[21] Appl. No.: 741,977

[22] Filed: Aug. 6, 1991

Related U.S. Application Data

[63] Continuation of Ser. No. 540,190, Jun. 19, 1990, abandoned.

[51] Int. Cl.$^5$ ............................................... C11D 1/18
[52] U.S. Cl. ................................. 252/547; 252/550; 252/DIG. 13; 424/70
[58] Field of Search ............... 252/547, DIG. 13, 550; 424/70

[56] References Cited

U.S. PATENT DOCUMENTS

| | | | |
|---|---|---|---|
| 2,771,395 | 11/1956 | Mehaffey | 167/87 |
| 3,931,033 | 1/1976 | Lohr et al. | 252/122 |
| 3,996,146 | 12/1976 | Tarasov et al. | 252/142 |
| 4,071,475 | 1/1978 | Iijima et al. | 252/545 |
| 4,126,674 | 11/1978 | Mausner | 424/31 |
| 4,165,369 | 8/1979 | Watanabe et al. | 424/70 |
| 4,247,538 | 1/1981 | Barker | 424/70 |
| 4,321,156 | 3/1982 | Bushman | 252/142 |
| 4,381,259 | 4/1983 | Homma et al. | 252/524 |
| 4,468,338 | 8/1984 | Lindberg | 252/105 |
| 4,469,627 | 9/1984 | Trombone | 252/548 |
| 4,544,495 | 10/1985 | Schmolka | 252/174 |
| 4,556,510 | 12/1985 | Holsopple | 252/547 |
| 4,701,322 | 10/1987 | Dixon et al. | 424/70 |
| 4,704,272 | 11/1987 | Oh et al. | 424/70 |
| 4,741,855 | 5/1988 | Grote et al. | 252/142 |
| 4,839,168 | 7/1989 | Abe et al. | 424/74 |
| 4,859,456 | 8/1989 | Marschner | 424/47 |
| 4,859,457 | 8/1989 | Suzuki et al. | 424/70 |
| 4,885,107 | 12/1989 | Wetzel | 252/106 |
| 4,931,216 | 6/1990 | Igarashi et al. | 252/547 |

OTHER PUBLICATIONS

"Lexquat AMG-BEO Clear Conditioning Shampoo SP-104", Inolex Chemicals, Nov., 1989.
"Celquat: Cationic Cellulose Polymers for cosmetics and toiletries", National Starch and Chemical Corporation, p. 9, 1982.
"Celquat H-100, L-200 Polymers—for cosmetics and toiletries", National Starch and Chemical Corporation, p. 4, 1988.
"Gafquat—Quaternary Polymers for the Cosmetic Industry", GAF Corporation Bulletin 2302-079, p. 3, 1980.
"Hair Conditioning Additives", Akzo Chemie Technical Brochure #89-139, p. 31, 1989.

Primary Examiner—Patrick P. Garvin
Assistant Examiner—E. D. Irzinski
Attorney, Agent, or Firm—Hayes, Soloway, Hennessey & Hage

[57] ABSTRACT

An optically clear aqueous conditioning shampoo and a process for preparing the same. The composition according to the invention comprises the combination of an anionic base detergent selected from the group consisting of sodium lauryl sulfate, potassium lauryl sulfate, ammonium lauryl sulfate and a cationic surface active conditioning agent whereby the conditioning agent is combined with the anionic shampoo base in an amount sufficient to avoid incompatibility and precipitation of the cationic and anionic components.

16 Claims, No Drawings

OPTICALLY CLEAR CONDITIONING SHAMPOO COMPRISING ANIONIC AND CATIONIC SURFACTANTS

This is a continuation of copending application Ser. No. 07/540,190, filed on Jun. 19, 1990.

TECHNICAL FIELD

The present invention relates to an aqueous conditioning shampoo and more particularly, to an optically clear composition which comprises a minor portion of non-polymeric cationic surface active agents and a major proportion of anionic cleansing agents. Such conditioning shampoos have good stability, cleansing, and high conditioning performance.

BACKGROUND OF THE INVENTION

The present invention is best put into perspective by the teachings of Anguillo et al, U.S. Pat. No. 3,816,616 (1974) which states in column 1 thereof, lines 20-52:

"The possibility of combining both shampoo and cream rinse action in a single composition for use in a single treatment of hair has been investigated by until now has been considered impractical. It is well known that anionic detergents and polymers are suitable for shampooing and that cationic detergents and polymers act as cream rinses in many instances. The difficulty which investigators have encountered where these two types of materials are contacted with one another is that they either precipitate or react with one another to the extent that their individual effectiveness is significantly impaired. This is so even if they remain in solution or in a suspended state. The incompatibility of anionic and cationic compounds is well recognized by workers in the art as indicated by Sagarin in *Cosmetics,* Interscience Publishers, New York, 1957, where it is stated on page 538 that anionic and cationic materials are not used in combination because they react to form salts. Thus, in practice, the anionic detergent shampoo is used first, followed by a separate cream rinse with a cationic material."

As a consequence, shampoos have since been prepared from foamy amphoteric compounds (having the capacity of behaving either as an acid or a base) and cationic compounds and cationic surface active agents. A separate cream rinse is applied, if desired, following rinsing of the shampoo composition from the hair, the cream rinse being used to condition the hair. This, of course, is time consuming and is not convenient. The results obtained in this matter also have not been fully satisfactory due to the difficulties associated with the deposition and retention on the hair of the hair conditioning aid. The inclusion of suitable hair conditioning agents in a shampoo therefore has certain attractive features.

For example, in U.S. Pat. No. 4,247,538 (1981) to Barker there is described an aqueous composition useful in shampooing and conditioning hair and containing an amphoteric shampoo base, a cationic surfactant and an anionic macrocolloid polymer (gum arabic). Upon rinsing, this composition deposited the macrocolloid polymeric component, providing desirable properties to the hair, such as body and curl retention.

Although such shampoos have been disclosed which contain conditioning aids, they have not been totally satisfactory for a variety of reasons. As noted, compatibility problems exist between good cleaning anionic surfactants and the fatty cationic agents which are good conditioning agents. This caused other surfactants, along with the amphoterics, to be considered by workers in the field, such as nonionics and zwitterionics. Others have attempted to carefully control pH in combination with polyethylene ester components, or neutralized fatty acids, which provided milder shampoo formulations. Such efforts are reflected in patents issued in the conditioning shampoo area. See, for example, U.S. Pat. No. 3,590,122 (1971) to Roberts et al; U.S. Pat. No. 3,808,329 to Bolich et al (1974); U.S. Pat. No. 3,849,348 (1974) to Hewitt; U.S. Pat. No. 3,990,991 (1976) to Gerstein; and U.S. Pat. No. 3,822,312 to Sato (1974).

More recently, U.S. Pat. No. 4,701,322 (1987) to Dixon et al described a conditioning shampoo where the conditioning agent is a saturated, straight chain fatty acid from about 14 to about 18 carbon atoms. U.S. Pat. No. 4,741,855 (1988) to Grote et al described conditioning shampoos which comprise a synthetic surfactant, an insoluble, non-volatile silicone, a suspending agent and water. This approach focused on maintaining a dispersed, insoluble silicon material in the aqueous shampoo medium by employing certain long chain acyl derivatives.

There have also been references to clear conditioning shampoos in various vendor brochures. For example, the water-white conditioning shampoo reported by Calgon is prepared via a batch mixing process combining 10.36% by weight of the active component of an anionic cleansing agent (sodium laureth-1-sulfate) with up to 0.8% by weight of the active component of the cationic conditioning agent Merquat 280 (a copolymer of dimethyldiallyl ammonium chloride and acrylic acid) and further incorporating cocomidopropyl betaine, sodium lauroyl sarcosinate, sodium chloride, fragrance and preservative. Citric acid is added to adjust the pH to 6.0. See Household and Personal Products Industries, 26(11), 16, (November 1989). The clear conditioning shampoo reported by Henkel is also prepared by a batch mixing process which combines 12.6% by weight of active ammonium lauryl sulfate with up to 0.9% by weight of a cationic conditioning agent hydroxycetyl hydroxyethyl dimonium chloride, further incorporating hydrolyzed animal protein as an additional conditioning component, cocamidopropyl amine oxide, fragrance, and preservative. The pH is adjusted to a range of 6.0 to 6.5 with citric acid. See the Product Information Bulletin, Henkel, Cospha Division, Clear Shampoo Conditioner Formula HOB-296-42-2.

While the above references disclose using anionic surfactants in combination with a cationic conditioning agent, they are not suggestive of compositions wherein through a particular combination of ingredients a clear product is produced which provides the functional properties of cleansing and conditioning the hair. Furthermore, the aforementioned references do not appreciate the limits of cationic conditioning agent that can be combined with an anionic cleansing agent to provide for an optically clear conditioning shampoo. In other words, the references fail to solubilize the now disclosed amounts of cationic conditioning agent per gram of anionic shampoo base detergent.

It is therefore an object of the present invention to provide a superior optically clear conditioning shampoo by incorporating the highest levels of cationic conditioning components in combination with anionic cleansing agents and avoiding problems of incompatibility and precipitation of the cationic and anionic compounds.

It is a further object of the present invention to provide a superior method wherein through a particular combination of anionic cleansing agents and cationic conditioning compounds problems of incompatibility and precipitation are avoided and an optically clear composition is produced.

A still further object of the present invention is to provide a superior method for cleaning and conditioning the hair.

Finally, the advantages of the present inventive combination include the convenience of treating the hair to a cleaning and conditioning action in a single step. Furthermore, the clarity of the system operates to clean and condition the hair without the use of insoluble fats, oils and waxes. The elimination of such insoluble components in the shampoo/conditioning matrix serves to provide a desired level of softness, good luster and manageability. These and other objects will become readily apparent from the detailed description which follows.

Unless otherwise indicated, all percentages and ratios herein are by weight.

SUMMARY OF THE INVENTION

The present invention relates to novel compositions useful for shampooing, cleaning and conditioning hair. More particularly, the instant discovery concerns optically clear aqueous conditioning shampoos which not only clean and shampoo but, upon rinsing, deposit a non-polymeric component on the hair which imparts very desirable properties to the hair, such as body, curl retention, superior dry feel and hair luster properties. The optically clear aqueous conditioning shampoo comprises the combination of an anionic base detergent selected from the group consisting of sodium lauryl sulfate, potassium lauryl sulfate, ammonium lauryl sulfate and a cationic surface active conditioning agent whereby the conditioning agent is combined with the anionic shampoo base in an amount sufficient to avoid incompatibility and precipitation of the cationic and anionic components. On a weight percent basis the shampoo and conditioning composition comprises about 0.1%–5.0% wetting agents, 0.1%–4.0% thickeners 9.75%–12.75% of the active components of the cleansing agent, 0.1%–1.62% of the active components of the conditioning agent, which are combined in a particular sequence to achieve the clear composition. When cleansing agents are supplied in the form of an aqueous solution, which provides both the active components of the cleansing agent in combination with water, the actual weight percentage of the cleansing agent may reach a level of about 35%–45%. This would be the case when the active components of the cleansing agent are supplied as an aqueous solution at an active component concentration of about 27%–28%. The weight ratio of the active cationic compounds to active cleansing agent ingredient is controlled not to exceed 1:6.8.

DETAILED DESCRIPTION

The essential components of the present invention are given in the following paragraphs:

Wetting Agent

An essential component of the present composition is a wetting agent. These are surface active agents which, when added to water, causes it to penetrate more easily into, or to spread over the surface of, another material by reducing the surface tension of the water. Examples include soaps, glycols, alcohols, and fatty acid compounds. Such agents generally are used individually at a level of from about 0.1% to about 5%, preferably from about 2.0% to about 3.0% by weight of the composition. In the most preferred embodiment the wetting agent comprises methoxy diglycol at a level of 2.5% by weight of the composition.

Thickener

The second essential ingredient in the conditioning shampoo is a water soluble, nonionic, cellulose polymer which functions both as a thickening agent, and as a conditioning agent. Suitable cellulosic polymers are selected from the group consisting of hydroxyethyl cellulose and hydroxypropyl methyl cellulose, with hydroxyethyl cellulose being preferred. Hydroxyethyl cellulose is the product of the reaction between an alkali cellulose and ethylene oxide, and such products are available in a number of viscosity grades. Viscosity is primarily dependent upon the viscosity of the cellulose used in the reaction. The moles of ethylene oxide per glucose unit are 2.0–2.8 and these hydroxyethyl celluloses have an average molecular weight range from about 80,000 to about 900,000. A particularly preferred hydroxyethyl cellulose is available under the trade name Natrosol 250 H from Aqualon, Inc. Water-soluble hydroxypropyl methyl cellulose has a methoxy content between about 25% and about 32% by weight and a hydroxypropyl content between about 2% and 10%, preferably 2% to about 7% by weight. Again, the chain length of the cellulose used in the reaction can be controlled to provide a molecular weight which yields a viscosity for a 2% solution in water in the range of 10 cps and 5000 cps, preferably 50 cps to 4000 cps. A particularly preferred hydroxypropyl methyl cellulose is available under the trade name Methocel F4M from Dow Chemical Company.

These cellulose polymers provide stability to the shampoo-conditioning formulation upon aging by viscosity control. The composition retains its viscosity without thinning out or thickening. In addition to controlling the viscosity of the aqueous shampoo-conditioner, the cellulose polymer contributes to its conditioning properties. It appears that hydrogen bonding occurs between the water soluble non-ionic cellulose polymer and the cationic quaternary compound, resulting in additional conditioning benefits to the shampoo-conditioner. This unexpected and dual function and coaction with the other essential conditioning ingredient, in a shampoo formulation, provides a uniquely superior shampoo-conditioning product. The combined cellulose polymer content constitutes about 0.1–4%, preferably 0.1 to 2%, most preferably the combination of 0.9% of hydroxyethyl cellulose and 0.1% of hydroxypropyl methyl cellulose, by weight, of the shampoo-conditioning hair rinse composition.

Cleansing Agents

The prime cleaning component of the composition of the present invention is the anionic detergent. Anionic detergents useful in the present invention are selected from the group of M-lauryl sulfate, and mixtures of M-lauryl sulfate together with a M-lauryl sulfate previously combined with 1–10 moles of ethylene oxide, wherein M is selected from sodium, potassium and ammonium. Ammonium lauryl sulfate and ammonium lauryl ether sulfate, alone or in combination are the most preferred cleansing agents for the present compositions. The total anionic detergent present in the composition in the present invention should be within the range of from 9.75%–12.75% by weight and particularly within the range from 11.2%–12.3% by weight of the active components of the anionic detergent. When mixtures of M-lauryl sulfate are used with other anionic detergents as described above, the mixture should be within the range of 0.1 to 0.2 parts anionic detergent per 1 part M-lauryl sulfate. The preferred M-lauryl sulfate for use in the composition of the present invention is ammonium lauryl sulfate. In the most preferred embodiment a mixture of ammonium lauryl sulfate (9.8% by weight of this active component) and ammonium lauryl ethersulfate (1.7% by weight of this active component) is employed.

Conditioning Agent

The cationic surface active agent of the invention is not limited to any specific ones. All cationic surface active agents which are normally used in hair rinse agents and exhibit at least partial solubility in water may be used in the practice of this invention. Preferable quaternary ammonium salts are those having the following formula (1):

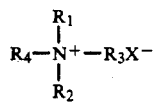

where $R_1$ and $R_2$ represent a lower alkyl group having 1 to 3 carbon atoms; $R_3$ represents a hydrogen or a lower hydroxyalkyl group having 1 to 4 carbon atoms; $R_4$ represents a hydroxyalkyl or hydroxyaryl or amido group having from about 8 carbons to about 20 carbons and X represents an anion from the halogen group. A particularly preferred compound is hydroxycetyl hydroxyethyl dimoniumchloride. The cationic quaternary ammonium compounds constitute about 0.1% to 1.65%, preferably 0.2% to 1.6%, most preferably 0.5% to 1.4% by weight of the active components of the conditioner portion of the shampoo/conditioner composition.

A critical requirement of the present invention is to maintain a significant excess of said ammonium salts in the mixture. For example, a mixture comprising 1.4% by weight of the active components of the conditioning agent and 11.5% by weight of the active components of the cleansing agent remains clear, while a mixture of 1.7% by weight of the active components of the conditioning agent and 11.5% by weight of the active components of the cleansing agent is cloudy, that is the conditioning agent precipitates. Therefore, the weight ratio of these cationic quaternary ammonium compounds to the cleansing agent ingredient should be controlled not to exceed 1:6.8, preferably 1:8.2.

Non-Volatile Silicone Fluid

Silicone fluids are a suitable non-volatile silicone that may be used in the present compositions as a further conditioning agent. The preferred non-volatile silicone fluid is a polyether siloxane copolymer and is present in a level of from about 0.1% to about 10.0% preferably from about 0.5% to about 5.0%, and in a most preferred embodiment, 2.0% of dimethyl silicone copolyol.

The essentially non-volatile polyether siloxane copolymer that may be used is, for example, a polypropylene oxide modified dimethylpolysiloxane (e.g. Dow Corning DC-1248) although ethylene oxide or mixtures of ethylene oxide and propylene oxide may also be used. Other non-volatile polyether silioxane copolymers that may be used include Dow Corning-190, 193 and Q2-5220, and Silwet L7001, L7500, L-7600, L-7602, L-7604 and L-7614 from Union Carbide Corporation.

References disclosing siloxane fluids include U.S. Pat. No. 2,826,551 to Green; U.S. Pat. No. 3,964,500 to Drakoff; U.S. Pat. No. 4,364,837 to Pader; British Patent No. 849,433 to Woolston and U.S. Pat. No. 4,741,855 to Grote and Russell. All of these patents are incorporated herein by reference to the extent that they refer to silcone copolyols. Also incorporated herein by reference is Silicon Compounds, distributed by Petrarch Systems, Inc., 1984. This reference provides a very good listing of suitable silcone materials.

Water

Water is the last essential component of the present invention and forms the remainder of the composition. It is generally present at a level of from about 20% to about 95%, preferably from about 40% to 95%, and in the most preferred embodiment, 75–85%. Note that these percentages of water reflect the weight percent of water relative to the weight percent of all active components.

Optional Components

The conditioning shampoos herein can contain a variety of non-essential optional components suitable for rendering such compositions more acceptable. Such conventional optional ingredients are well known to those skilled in the art, e.g. preservatives such as benzyl alcohol, methyl paraben, propyl paraben, imidazolidinyl urea, methylchloroisothiazolinone and methylisothiazolinone; thickeners and viscosity modifiers such as coconut ethanolamide, sodium chloride, ammonium chloride, sodium sulfate, carboxymethyl cellulose, methyl cellulose, polyvinylalcohol, and ethyl alcohol; perfumes; dyes, sequestering agents such as disodium ethylenediamine tetraacetate; pH adjusting agents such as citric acid, succinic acid, phosphoric acid, sodium hydroxide, sodium carbonate, etc.; and a foam booster such as lauric diethanolamide.

Method of Manufacture

The optically clear shampoo/conditioning composition of the invention cannot be obtained merely by mixing the previously mentioned ingredients at the indicated or preferred concentrations in the defined ranges of amounts of water. In order to obtain the optically clear shampoo/conditioning composition of the invention, the wetting agent and majority of thickener are added to water, followed by heating under agitation to a temperature of about 70° C. with further addition of the remaining amount of thickener compound. At this point the mixture normally appears cloudy, owing to limited solubilization or precipitation of the thickener component. The mixture is then allowed to cool to room temperature. The cleansing agents, or blend thereof, is then added at which point it appears that any insoluble thickener becomes completely solubilized. The conditioning agent is then added followed by addition of preservative and further conditioning agents such as the non-volatile silicone fluids. Thereafter, optional components such as preservatives, viscosity modifiers, sequestering agents, pH adjusting agents and a foam booster may be added to complete the formulation.

INDUSTRIAL APPLICABILITY

The present compositions are used in a conventional manner for cleaning and conditioning hair. Such shampoo/conditioner compositions of the invention are stable under either low temperature or high temperature conditions, with very good shampoo/conditioning performance. For example, although the inventive composition turns cloudy and solidifies at temperatures below 15° C., it becomes transparent with complete shampoo/conditioning performance upon subsequent warming. Exposure to elevated temperatures may effect the final viscosity of the formulation, but again the shampoo/conditioning performance returns and remains functional upon cooling. In its method aspect, the present invention comprises a method of shampooing the hair by contacting the hair with an amount of the shampoo/conditioner compositions herein which is effective to clean and condition the hair and serves to rinse the cleansing agents from the hair. An effective amount for any individual will depend on variable factors such as the length of the hair, thickness of the hair, amount of soil present, etc. Generally, an effective amount will be from about 5 to 40 grams per use.

The following Examples further describe and demonstrate the preferred embodiments within the cope of the present invention. The Examples are given solely for the purpose of illustration and are not to be construed as limitations of the present invention as many variations thereof are possible without departing from its spirit and scope.

Examples I-V

The following compositions are representative of the present invention. All amounts of various ingredients in the examples, as well as elsewhere in the specification, are by weight unless otherwise specified.

| INGREDIENT | EXAMPLES | | | | |
|---|---|---|---|---|---|
| | I | II | III | IV | V |
| Water | 80.35 | 79.95 | 79.65 | 82.85 | 80.75 |
| Methoxydiglycol | 2.50 | 2.50 | 2.50 | — | 2.50 |
| Hydroxyethyl Cellulose | 0.90 | 0.90 | 0.90 | 0.90 | 0.50 |
| Hydroxypropyl Methyl Cellulose | 0.10 | 0.10 | 0.10 | 0.10 | 0.10 |
| Ammonium Lauryl Sulfate | 9.80 | 9.80 | 9.80 | 9.80 | 9.80 |
| Ammonium Laurylether Sulfate | 1.70 | 1.70 | 1.70 | 1.70 | 1.70 |
| Hydroxycetyl Hydroxyethyl Dimonium Chloride | 1.00 | 1.40 | 1.70 | 1.00 | 1.00 |
| Methylchlorisothiazolinone and Methylisothiazolinone | 0.10 | 0.10 | 0.10 | 0.10 | 0.10 |
| Dimethicone Copolyol | 2.00 | 2.00 | 2.00 | 2.00 | 2.00 |
| Citric Acid | 0.05 | 0.05 | 0.05 | 0.05 | 0.05 |
| Lauric Diethanolamide | 1.50 | 1.50 | 1.50 | 1.50 | 1.50 |

The compositions of Example I were preferred over each of the comparative examples. Furthermore, Example II exhibits a higher level of conditioner. Example III exhibits a level of conditioner that inhibits the clarity of the formulation. Example IV also exhibits a formulation that does not have maximum optical clarity. Finally, Example V exhibits reduced conditioning qualities due to lower levels of hydroxyethyl cellulose.

What is claimed is:

1. An optically clear aqueous conditioning shampoo which comprises the combination of:

a. an anionic shampoo base detergent compound selected from the group consisting of sodium lauryl sulfate, sodium lauryl ether sulfate, potassium lauryl sulfate, ammonium lauryl sulfate, ammonium lauryl ether sulfate and mixtures thereof; and b. a cationic surface active conditioning agent wherein the cationic active agent comprises a hydrophilic cationic quaternary ammonium salt having the following formula:

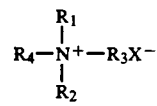

wherein $R_1$ and $R_2$ represent a lower alkyl group having 1 to 3 carbon atoms; $R_3$ represents a hydrogen or a lower hydroxyalkyl group having 1 to 4 carbon atoms; $R_4$ represents a 8 to 20 carbon atom hydroxyalky, hydroxyaryl or amido group, and X represents a halogen group, wherein the weight ratio of the active ingredients in the cationic active surface active agent to the anionic shampoo base detergent is controlled between about 1:11,5 to 1:6.8.

2. The optically clear aqueous conditioning shampoo composition according to claim 1 further comprising at least one material related from the group consisting of a wetting agent, a thickener, a non-volatile silicone fluid, a preservative, a viscosity modifier, a dye, a sequestering agent and a pH adjusting agent, and mixtures of one or more of said materials.

3. The optically clear aqueous conditioning shampoo composition of claim 2 wherein the wetting agent is selected from the group consisting of a soap, a glycol, an alcohol, a fatty acid compound and mixtures thereof, and is present at a level of about 1-3% by weight.

4. The optically clear aqueous conditioning shampoo composition of claim 3 wherein the wetting agent comprising methoxy diglycol and is present at a level of 2.5% by weight.

5. The optically clear aqueous conditioning shampoo composition according to claim 2 wherein the thickener is a water soluble, nonionic cellulose polymer selected from the group consisting of hydroxyethyl cellulose, hydroxypropyl methyl cellulose and mixtures thereof, and is present at a level of about 0.1% to 4.0% by weight.

6. The optically clear aqueous conditioning shampoo composition according to claim 2 wherein the thickener comprises 0.9% by weight of hydroxyethyl cellulose and 0.1% by weight of hydroxypropyl methyl cellulose.

7. The optically clear aqueous conditioning shampoo composition according to claim 1 wherein the non-volatile silicon fluid comprises a polyethersiloxane and is present at a level of about 0.1% to about 10.0% by weight.

8. The optically clear aqueous conditioning shampoo composition according to claim 7 wherein the non-volatile silicone fluid comprises 2.0% by weight dimethyl silicon copolyol.

9. The optically clear aqueous conditioning shampoo composition according to claim 1 wherein the preservative is selected from the group consisting of benzyl alcohol, methyl, paraben, propyl paraben, imidazolidinyl urea, methylchloroisothiazolinone, methylisothiazolinone, and mixtures thereof, and is present at a level of about 0.1% by weight.

10. The optically clear aqueous conditioning shampoo composition according to claim 2 wherein the viscosity modifier is selected from the group consisting of coconut ethanol amide, sodium chloride, ammonium chloride, sodium sulfate, carboxymethyl cellulose, methyl cellulose, polyvinylalcohol, ethyl alcohol and mixtures thereof, and is present at a level of about 1.0%-3.0% by weight.

11. An optically clear aqueous conditioning shampoo which comprises, by weight of active ingredients based upon the total weight of the composition:
   a. from about 9.5% to about 12.6% of an anionic shampoo base detergent, selected from the group consisting of sodium lauryl sulfate, sodium lauryl ether sulfate, potassium lauryl sulfate, ammonium lauryl sulfate, ammonium lauryl ether sulfate and mixtures thereof; and
   b. from about 1.0% to about 1.7% of a cationic surface active agent selected from the group consisting of a compound of the following formula:

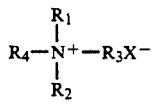

wherein $R_1$ and $R_2$ represent a lower alkyl group having 1 to 3 carbon atoms; $R_3$ represents a hydrogen or a lower hydroxyalkyl group having 1 to 4 carbon atoms; $R_4$ represents a 8 to 20 carbon atom hydroxyalky, hydroxyaryl or amido group, and X represents a halogen group, wherein the weight ratio of the active ingredients in the cationic active surface active agent to the anionic shampoo base detergent is controlled between about 1:11.5 to 1:6.8.

12. The optically clear aqueous conditioning shampoo of claim 11 comprising an active component mixture of 9.8% ammonium lauryl sulfate and 1.68% ammonium lauryl ethersulfate as the anionic shampoo base with 1.4% hydroxycetyl hydroxyethyl dimethylammonium chloride as the cationic conditioning agent.

13. A process for preparing the optically clear aqueous conditioning shampoo comprising:
   a. preparing an aqueous solution of about 1-3% by weight of a wetting agent selected from the group consisting of a soap, a glycol, an alcohol a fatty acid compound and mixtures thereof, with the majority of at least one thickener compound;
   b. heating under agitation to a temperature of about 70° C. with the addition of the remaining amount of said thickener compound;
   c. cooling to room temperature;
   d. thereafter adding an anionic shampoo base detergent selected from the group consisting of sodium lauryl sulfate, sodium lauryl ether sulfate, potassium lauryl sulfate, ammonium lauryl sulfate, ammonium lauryl ether sulfate and mixtures thereof;
   e. thereafter adding the cationic surface active conditioning agent in an amount sufficient to avoid incompatibility and precipitation of the cationic surface active conditioning agent with the anionic shampoo base detergent wherein the cationic active agent comprises a hydrophilic cationic quaternary ammonium salt having the following formula:

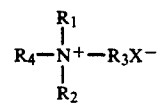

wherein $R_1$ and $R_2$ represent a lower alkyl group having 1 to 3 carbon atoms; $R_3$ represents a hydrogen or a lower hydroxyalkyl group having 1 to 4 carbon atoms; $R_4$ represents a 8 to 20 carbon atom hydroxyalkyl, hydroxyaryl or amido group, and X represents a halogen group, wherein the weight ratio of the active ingredients in the cationic active surface active agent to the anionic shampoo base detergent is controlled between about 1:11.5 to 1:6.8.

14. The process of claim 13 whereby the wetting agent is methoxy diglycol and is present at a level of 2.5% by weight, the thickener is present at a level of about 0.1% to 4.0% by weight, the anionic shampoo base detergent is present at a level of about 9.8% to about 12.6% by weight of active component, and the cationic surface active conditioning agent is present at a level of about 1.0%-1.7% by weight of active component.

15. The process of claim 13 wherein the weight ratio of the cationic surface active agent to the anionic shampoo base detergent is controlled not to exceed 1:6.8.

16. The process of claim 13 with the additional step of adding to the optically clear aqueous shampoo composition a material selected from the group consisting of a non-volatile silicone fluid, a preservative, a viscosity modifier, a dye, a sequestering agent a pH adjuster, and mixtures of one or more of said materials.

* * * * *

UNITED STATES PATENT AND TRADEMARK OFFICE
CERTIFICATE OF CORRECTION

PATENT NO. : 5,145,607

DATED : SEPTEMBER 8, 1992

INVENTOR(S) : ARTHUR G. RICH

It is certified that error appears in the above-identified patent and that said Letters Patent is hereby corrected as shown below:

Claim 1, Col. 8, line 25, "1:11,5" should be --1:11.5--.

Signed and Sealed this

Seventh Day of December, 1993

Attest:

BRUCE LEHMAN

*Attesting Officer*        *Commissioner of Patents and Trademarks*